United States Patent [19]
Foser

[11] Patent Number: 5,833,464
[45] Date of Patent: Nov. 10, 1998

[54] METHOD FOR MANUFACTURING A CERAMIC DENTAL REPLACEMENT

[75] Inventor: Hans Peter Foser, Balzers, Liechtenstein

[73] Assignee: Ivoclar A.G., Schaan, Liechtenstein

[21] Appl. No.: 900,475

[22] Filed: Jul. 25, 1997

Related U.S. Application Data

[60] Provisional application No. 60/031,129 Nov. 18, 1996.

[30] Foreign Application Priority Data

Jul. 26, 1996 [DE] Germany .......................... 196 30 412.1

[51] Int. Cl.$^6$ ...................................................... A61C 5/00
[52] U.S. Cl. ........................ 433/228.1; 433/220; 433/225
[58] Field of Search .............................. 433/200.1, 201.1, 433/202.1, 212.1, 218, 222.1, 224, 225, 228.1, 220

[56] References Cited

U.S. PATENT DOCUMENTS

| | | | |
|---|---|---|---|
| 4,351,853 | 9/1982 | Jochua et al. ................. | 433/201.1 X |
| 4,828,495 | 5/1989 | Bell et al. ..................... | 433/200.1 |
| 4,936,776 | 6/1990 | Kwaitkowski . | |
| 5,062,798 | 11/1991 | Tsuge et al. .................. | 433/201.1 |
| 5,125,971 | 6/1992 | Nonami et al. ............... | 433/228.1 X |
| 5,346,396 | 9/1994 | Hakamatsuka ................ | 433/208 |
| 5,698,019 | 12/1997 | Frank et al. .................. | 433/212.1 X |

FOREIGN PATENT DOCUMENTS

| | | |
|---|---|---|
| 0 231 773 | 1/1987 | European Pat. Off. . |
| 0 695 726 | 7/1995 | European Pat. Off. . |
| 32 48 649 | 7/1983 | Germany . |
| 42 10 781 | 4/1995 | Germany . |
| 44 23 794 | 2/1996 | Germany . |
| 08157319 | 6/1996 | Japan . |

OTHER PUBLICATIONS

M. Simon, "Neus Perspektiven zur volkeramischen Stabilsierung und zum Aufbau devitaler Zahne", Quintessenz 46, pp. 1085–1101 (1995).

D. Kaelin and P. Scarer, "Aufbausysteme in der Kronen–und Bruckenprothetik", Schweiz Monatsschr. Zahnmed. vol. 101, pp. 457–463 (1991).

K. H. Meyenberg, H. Luthy, and P. Scharer, "Zirconia Posts; A New All Ceramic Concept for Nonvital Abutment Teeth", Journal of Esthetic Dentistry, vol. 7, No. 2, pp. 73–80, (1995).

*Primary Examiner*—Nicholas D. Lucchesi
*Attorney, Agent, or Firm*—John C. Thompson; Alan S. Korman

[57] ABSTRACT

A method for manufacturing a ceramic dental replacement includes providing a pin and attaching a ceramic material to the pin to form a ceramic body. The thermal expansion coefficient of the pin, measured at 20° C. to 500° C. is selected to be identical to or up to 3.0 $\mu$m/mK greater than a thermal expansion coefficient of the ceramic body, measured at 20° C. to 500° C.

20 Claims, No Drawings

METHOD FOR MANUFACTURING A CERAMIC DENTAL REPLACEMENT

This application claims priority of provisional application 60/031,129 filed Nov. 18, 1996.

BACKGROUND OF THE INVENTION

The present invention relates to a method for manufacturing a ceramic dental replacement comprised of a $ZrO_2$ pin and a $ZrO_2$ ceramic glass material, to a ceramic dental replacement as described, and to its use.

In the past, metallic pins and metallic base materials have been used as pin-based dental replacements, because of special material properties and because of manufacturing considerations. Such conventional pin-based systems are, for example, known from M. Simon, "Neue Perspektiven zur vollkeramischen Stabilisierung und zum Aufbau devitaler Zähne", Quintessenz 46, pages 1085–1101 (1995) and from: D. Kaelin und P. Scarer, "Aufbausysteme in der Kronen- und Brückenprothetik", Schweiz Monatsschr. Zahnmed. Vol. 101. pp. 457–463 (1991). The covering of the substructure with plastic or ceramic was then separately carried out. The known solutions however exhibit a series of problems, for example, corrosion of certain metals or metal alloys and their deposit in the surrounding tissue, inflammation of the gingiva or dark discolorations of the surrounding soft and hard tissue due to the opaque properties of metallic materials. For these reasons, in the recent past metal constructions have been used less and less, while transparent materials with an improved visual appearance and biocompatibility have been used increasingly.

Zirconium dioxide pins have an especially high mechanical strength as disclosed, for example, in K. H. Meyenberg, H. Lüthy and P. Schärer, "Zirconia Posts: A New All Ceramic Concept for Nonvital Abutment Teeth", Journal of Esthetic Dentistry, Vol. 7, No. 2, (1995) and the aforementioned reference Quintessenz 46, 1085–1101, (1995). For manufacturing dental replacements the $ZrO_2$ root pin is inserted and a composite construction is attached. In the dental laboratory a crown, for example, of IPS Empress Keramik (trademark of Ivoclar, Schaan, Liechtenstein) is manufactured and attached in a conventional manner, for example, with an adhesive system and a transparent composite cement. Such solutions have a very good biocompatibility because metallic materials have been avoided. However, an improved strength would be desirable.

From U.S. Pat. No. 4,936,776 different dental replacements of transparent porcelain ceramic materials are known. According to one embodiment, to a transparent ceramic pin a porcelain ceramic is fused (by firing in a furnace). However, the construction disclosed in U.S. Pat. No. 4,936,776 with the fused porcelain ceramic crown exhibits low load resistance due to a low breaking resistance.

It has also been suggested to fuse to a known metal pin a ceramic construction and to cement thereto a ceramic crown. However, this design exhibits the problem of tension fractures within the ceramic, as has been disclosed in the aforementioned reference Schweiz. Monatsschr. Zahnmed. Vol. 101 (1991).

It is therefore an object of the present invention to provide, while avoiding the disadvantages of the prior art, a method for manufacturing a ceramic dental replacement comprised of a high strength pin, especially a $ZrO_2$ pin, and a ceramic base body fused thereto, especially a $ZrO_2$ ceramic glass material with excellent mechanical properties whereby it is desired to produce very stable and securely fused dental replacements having excellent strength, especially flexural strength and tensile strength, without exhibiting tensional fractures.

SUMMARY OF THE INVENTION

A method for manufacturing a ceramic dental replacement includes the following steps:

providing a pin;

attaching a ceramic material to the pin to form a ceramic body on the pin;

selecting a thermal expansion coefficient of the pin, measured at 20° C. to 500° C. to be identical or up to 3.0 $\mu$m/mK greater than a thermal expansion coefficient of the ceramic body, measured at 20° C. to 500° C.

The thermal expansion coefficient of the pin is up to 2.0 $\mu$m/mK greater than the thermal expansion coefficient of the ceramic body.

The method may further include a step of preparing the pin of $ZrO_2$.

Advantageously, the method further includes the step of preparing the pin of a ceramic material.

Advantageously, the method further includes a step of selecting a $ZrO_2$ ceramic glass material for the ceramic body.

Preferably, the thermal expansion coefficient of the pin is 0.2 to 2.0 $\mu$m/mK greater than the thermal expansion coefficient of the ceramic body.

The thermal expansion coefficient of the pin is about 11 $\mu$m/mK and the thermal expansion coefficient of the ceramic body is about 9.5 $\mu$m/mK.

Advantageously, a $ZrO_2$ glass blank is used as the ceramic material, whereby the blank has a melting point that is lower than the melting point of the pin.

In the step of attaching, the ceramic material is directly fused onto the pin.

Advantageously, the step of attaching includes heating the ceramic material for plasticizing the ceramic material, thereafter pressing the ceramic material into a mold, sintering the ceramic material in the mold, and cooling the ceramic material.

Preferably, the step of pressing is performed at a temperature of 1000° C. or less.

The step of attaching may include:

preparing a precisely sized model of the dental replacement of the pin and of a meltable molding material;

applying a strand of the meltable molding material to the model;

placing the model and the strand into a curable potting compound;

heating the meltable molding material for removing the meltable molding material from the potting compound such that a mold for the ceramic body is formed, wherein the removed strand leaves behind a casting channel in the potting compound;

introducing the ceramic material into the mold through the casting channel;

arranging a piston at the casting channel and pressurizing the ceramic material by the piston for pressing the ceramic material under thermal plasticization into the mold.

Advantageously, the step of pressing is performed at a temperature of 1000° C. or less.

The pin is a prefabricated, partially stabilized $ZrO_2$ pin.

The pin preferably has a flexural strength of at least 600 MPa preferably of 800 to 1500 MPa.

The ceramic dental replacement preferably has a flexural strength of least 100 MPa.

The present invention also relates to a ceramic dental replacement comprised of a $ZrO_2$ ceramic glass body and a $ZrO_2$ pin, wherein the thermal expansion coefficient of the pin, measured at 20° C. to 500° C., is identical to or up to 3.0 μm/mK greater than a thermal expansion coefficient of the ceramic glass body measured at 20° C. to 500° C.

The invention also related to a method of using the ceramic dental replacement described above for reconstructing missing tooth substance of vital and non-vital teeth. Preferably, a root, a crown, a neck, or the crown and neck of a tooth are reconstructed with the inventive method.

A special advantage of the present invention is that an excellent overall strength of the dental replacement can be achieved without having to use metal pins of high strength that have been used in the past and without having to contend with the aforementioned disadvantages, for example, insufficient biological compatibility, unsatisfactory aesthetical appearance, corrosion etc.

The inventively produced dental replacement exhibit in addition to excellent biological compatibility, an excellent aesthetical appearance, very similar to the appearance of a natural tooth. They also have a very good strength properties. The excellent physical properties can be related to a plurality of factors. First of all, the use of $ZrO_2$ pins results in an especially great flexural strength of the dental replacement within the tooth root. Furthermore, by using $ZrO_2$ ceramic glass materials the dental replacement facing the tooth crown also exhibits an especially high mechanical loading resistance.

Furthermore, the inventive selection of the thermal expansion coefficient of the $ZrO_2$ pin and the $ZrO_2$ ceramic glass material due to their material compatibility in connection with the pressing step, results in an especially intimate stable fusing or connection.

In comparison to conventional adhesive connections, respectively, cementing, the overall stability of the dental replacement is considerably increased. Not only the excellent adhesion between $ZrO_2$ and $ZrO_2$-containing ceramic glass materials is taken advantage of. Since the application of the $ZrO_2$ ceramic glass material is carried out under pressure, the intimate connection of the two components is reinforced. The pressing action of the $ZrO_2$ ceramic glass material into the pin can only be effective when the thermal expansion coefficient of the $ZrO_2$ pin corresponds at least substantially to that of the $ZrO_2$ ceramic glass material.

An especially advantageous and surprising effect results when the $ZrO_2$ pin upon cooling due to the higher heat expansion coefficient, will contract to a greater extent than the surrounding $ZrO_2$ ceramic glass material. Thus results, after the $ZrO_2$ ceramic glass material has been pressed onto the $ZrO_2$ pin, a certain tension results between the two components whereby the $ZrO_2$ ceramic glass material pressed onto the $ZrO_2$ pin due to the contraction of the pin, is pressurized (tensioned) similar to reinforced concrete.

It was surprisingly found that this improves the mechanical properties of the ceramic dental replacement. For example, the inventive dental replacements have an excellent overall flexural strength, exhibit no tensional fractures and, in general, have an especially high resistance to the forces acting onto dental replacements during chewing. Surprisingly, the inventive stiffness and strength is ensured despite the different material selection for the $ZrO_2$ pin and the $ZrO_2$ ceramic glass material used for the ceramic body. The overall flexural strength is the strength exhibited by the $ZrO_2$ pin with fused $ZrO_2$ ceramic glass body.

For a certain difference between the thermal expansion coefficients of the $ZrO_2$ pin and the $ZrO_2$ ceramic glass material fractures may occur during pressing. This critical difference between the thermal expansion coefficients depends in individual cases on the selected $ZrO_2$ ceramic glass material and the selected $ZrO_2$ pin. In general, however these problems will not occur when the thermal expansion coefficient of the $ZrO_2$ pin is more than approximately 2 μm/mK above the thermal expansion coefficient of the $ZrO_2$ ceramic glass material or the difference between the thermal expansion coefficients should, in general, be greater than 2 μm/mK.

A further advantage of the invention is the savings in time because of the manufacture of the complete dental replacement during the firing process. Accordingly, a separate cementing or adhesive attachment of the ceramic body onto the pin to be inserted into the root is avoided. Furthermore, sometimes occurring negative patient reactions to the used materials can be avoided. Finally, the inventively produced dental replacements have an especially pleasing aesthetic appearance because they are very similar to a natural tooth, have a continuous translucent structure in one piece and can thus be matched as closely as possible to the visual appearance of natural dentin, respectively, tooth enamel.

Dental replacement, in the context of the present invention, relates to any shaped tooth replacement construction that includes a combination of a pre-fabricated or individually formed pin with any suitable ceramic body selected depending on the intended use of the dental replacement, i.e., a partial or a full dental crown.

It was found that the inventive advantages can be realized especially easily when the thermal expansion coefficient of the $ZrO_2$ pin is 0.5 to 2.0 μm/mK above the thermal expansion coefficient of the $ZrO_2$ ceramic glass material.

According to a preferred embodiment the $ZrO_2$ pin has a thermal expansion coefficient of approximately 11 μm/mK and the $ZrO_2$ ceramic glass material has a heat expansion coefficient of approximately 9.5 μm/mK.

Inventively, $ZrO_2$ pins are defined as ceramic (root) pins made of zirconium dioxide which, however, can also be partially stabilized with yttrium oxide (approximately 3 to 4 weight-% $Y_2O_3$). Such ceramic materials result in an especially good adhesion to the $ZrO_2$-containing ceramic glass materials.

In the present invention it is possible to use any suitable $ZrO_2$-containing ceramic glass material with sufficient mechanical properties and respectively selected thermal expansion coefficients. For example, the $ZrO_2$ ceramic glass materials disclosed in German Patent 44 23 794 are suitable, and the disclosure of this patent is enclosed by reference in this specification.

In a preferred embodiment the pressing of the $ZrO_2$ceramic glass material is carried out in a ceramic pressing method whereby the $ZrO_2$ ceramic glass material may be present initially in the form of a blank.

It was found that for the instant invention especially good results can be achieved when during the ceramic pressing method the $ZrO_2$ ceramic glass material is provided in the form of a ceramic blank that is plasticized by heating, is pressed under pressure into the hollow mold, sintered and hardened during cooling. This ensures that the $ZrO_2$ ceramic glass material can be pressed in the plasticized state especially well onto the $ZrO_2$ pin and that during subsequent sintering and cooling an especially intimate connection is formed so that the aforementioned advantageous effects can be realized by applying pressure during manufacturing.

The ceramic pressing method disclosed in European Patent Application 0 231 773 and the furnaces used in connection therewith provide very good results in connection with the inventive method. With respect to a more detailed description of the method and the furnaces used in this content, the disclosure of the European Patent Application is herewith incorporated by reference into the specification. Such a method, respectively, such devices are for example, also used in the IPS-Empress method (trade of Ivoclar, Shaan, Liechtenstein).

For example, a typical inventive method may include the following method steps whereby, depending on the intended use, it is possible to incorporate suitable modifications.

1. Impression of the patients mouth with inserted ceramic root pin;
2. Manufacture of a model from the impression, whereby the pin projects from the model;
3. Shaping a tooth reconstruction of a meltable molding material, preferably wax or plastic, on the pin (for example in the form of a crown stump or a partial or full dental crown);
4. Applying a wax pin or a strand which later on will provide the casing channel;
5. Embedding pin and wax parts into a muffle furnace with a curable potting material;
6. Removing the wax, respectively, the meltable molding material by heating;
7. Performing the actual ceramic pressing method, for example, according to European Patent Application 0 231 773, whereby the $ZrO_2$ ceramic glass material is introduced via the casting channel (in the form of a blank), is plasticized by heating, and pressurized by a piston provided at the casing channel, and is hardened during cooling whereby the $ZrO_2$ pin has a thermal expansion coefficient that is at most twice as high as the thermal expansion coefficient of the $ZrO_2$ ceramic glass material.

pressure can be applied with a constant value or with changing values or also by intermittent application.

It is especially advantageous that in the inventive method relatively low firing temperatures are used, in general below 1200° C., preferably even below 1000° C. This allows for a favorable and inexpensive method.

Furthermore, less complicated furnaces are sufficient and the heating period is reduced.

In a preferred embodiment of the invention the $ZrO_2$ pin has flexural strength of at least 600 MPa, especially of 800 to 1500 MPa. Thus, the used $ZrO_2$ pins in their flexural strength are within the range of highly resistance, conventionally used metal pins or exhibit even greater strength. In the inventively manufactured ceramic dental replacements this high flexural strength is especially favorable with respect to the overall flexural strength of the dental replacements so preferably overall flexural strengths of at least 100 MPa can be achieved.

According to a further aspect of the invention a dental replacement, preferably manufactured according to the method disclosed herein, is also claimed.

According to another aspect, the present invention also relates to the use of a ceramic dental replacement as a dental product. Furthermore, the method of use includes any suitable application within dentistry, for example, the reconstruction of missing hard tooth parts in vital or non-vital teeth. Conventional applications include dental reconstructions such as tooth root reconstruction with partial or full dental crowns.

DESCRIPTION OF PREFERRED EMBODIMENT

The present invention will now be described in detail with aid of a particular embodiment.

A Biopost root pin (trademark of Incermed S.A., Lausanne, Switzerland) of the suitable size made of zirconium dioxide was used. The pin was introduced into the conventionally prepared root canal and an impression of the patient's mouth was taken. Subsequently, a model of a superhard gypsum material was produced from the impression whereby the pin projects from the model. Based on this model, a crown of wax was modeled onto the pin whereby the wax was a material than can removed by heating without leaving any residue. The pin was conditioned with $Al_2O_3$.

The model was then introduced into an IPS-Empress muffle base (trademark of Ivoclar). It is possible to position a plurality of such models onto the base of the muffle furnace whereby the spacing between the models in this technique must be at least 3 mm. Subsequently, the muffle base was enclosed by a paper cylinder and the models including the $ZrO_2$ pins were embedded into an IPS-Empress potting compound. After the prescribed curing time, the muffle enclosure and the muffle base were removed by a rotational movement and the paper enclosure was removed, whereby it was ensured that no potting material remains within the casting channel.

The thus prepared muffle was introduced into a preheating furnace and preheated together with a AlOx-piston as disclosed in the manual of IPS-Empress published by Ivoclar. The $ZrO_2$ blank was heated separately. The $ZrO_2$ ceramic glass material is of the composition disclosed in German Patent 44 23 794 in Example 1 and has the following weight percent composition (in parentheses); $SiO_2$ (52.8), $Al_2O_3$ (3.0), $Li_2O$ (12.9), $P_2O_5$ (10.4), $ZrO_2$ (20.9). After completion of the preheating phase the $ZrO_2$ glass ceramic blank was inserted into the casing channel and subsequently the AlOx piston was inserted into the casing channel. The ceramic pressing method was performed at 950° C. and a pressure of 5 bar. After cooling, the object (dental replacement) was removed in a conventional manner from the muffle and cleaned. It could be directly introduced into the tooth cavity, optionally after small shape corrections, painting, and glazing.

The present invention is, of course, in no way restricted to the specific disclosure of the specifications, and drawings, but also encompasses any modifications within the scope of the appended claims.

What is claimed is:

1. A method for manufacturing a ceramic dental replacement, said method comprising the steps of:
   providing a pin;
   attaching a ceramic material to said pin to form a ceramic body on said pin;
   selecting a thermal expansion coefficient of said pin, measured at 20° C. to 500° C., to be identical to or up to 3.0 $\mu$m/mK greater than a thermal expansion coefficient of said ceramic body, measured at 20° C. to 500° C.

2. A method according to claim 1, wherein said thermal expansion coefficient of said pin is up to 2.0 $\mu$m/mK greater than said thermal expansion coefficient of said ceramic body.

3. A method according to claim 1, further including a step of preparing said pin of $ZrO_2$.

4. A method according to claim 1, further including a step of preparing said pin of a ceramic material.

5. A method according to claim 1, further including a step of selecting a $ZrO_2$ ceramic glass material for said ceramic body.

6. A method according to claim 1, wherein said thermal expansion coefficient of said pin is 0.5 to 2.0 $\mu$m/mK greater than said thermal expansion coefficient of said ceramic body.

7. A method according to claim 1, wherein said thermal expansion coefficient of said pin is about 11 μm/mK and wherein said thermal expansion coefficient of said ceramic body is about 9.5 μm/mK.

8. A method according to claim 1, wherein in said step of attaching a $ZrO_2$ glass blank, having a melting point that is lower than a melting point of said pin, is selected as said ceramic material.

9. A method according to claim 1, wherein in said step of attaching said ceramic material is directly fused onto said pin.

10. A method according to claim 9, wherein said step of attaching includes heating said ceramic material for plasticizing said ceramic material, thereafter pressing said ceramic material into a mold, sintering said ceramic material in said mold, and cooling said ceramic material.

11. A method according to claim 10, wherein said step of pressing is performed at a temperature of 1000° C. or less.

12. A method according to claim 9, wherein said step of attaching includes:

preparing a precisely sized model of said dental replacement of said pin and of a meltable molding material;

applying a strand of said meltable molding material to said model;

placing said model and said strand into a curable potting compound;

heating said meltable molding material for removing said meltable molding material form said potting compound such that a mold for said ceramic body is formed, wherein the removed strand leaves behind a casting channel in said potting compound;

introducing said ceramic material into said mold through said casting channel;

arranging a piston at said casting channel and pressurizing said ceramic material by said piston for pressing said ceramic material under thermal plasticization into said mold.

13. A method according to claim 12, wherein said step of pressing is performed at a temperature of 1000° C. or less.

14. A method according to claim 1, wherein said pin is a prefabricated, partially stabilized $ZrO_2$ pin.

15. A method according to claim 1, wherein said pin has a flexural strength of at least 600 MPa.

16. A method according to claim 15, wherein said pin has a flexural strength of 800–1500 MPa.

17. A method according to claim 1, wherein said ceramic dental replacement has a flexural strength of at least 100 MPa.

18. A ceramic dental replacement comprised of a $ZrO_2$ ceramic glass body and a $ZrO_2$ pin, wherein a thermal expansion coefficient of said pin, measured at 20° C. to 500° C., is identical to or up to 3.0 μm/mK greater than a thermal expansion coefficient of said ceramic glass body, measured at 20° C. to 500° C.

19. A method of using a ceramic dental replacement comprised of a $ZrO_2$ ceramic glass body and a $ZrO_2$ pin, wherein a thermal expansion coefficient of said pin, measured at 20° C. to 500° C., is identical to or up to 3.0 μm/mK greater than a thermal expansion coefficient of said ceramic glass body, measured at 20° C. to 500° C., comprising the steps of obtaining and dental replacement, and reconstructing missing tooth substance of vital and non-vital teeth.

20. A method according to claim 19 wherein said step of reconstructing is used for reconstructing a root, a crown, a neck, or a crown and a neck of a tooth.

* * * * *